(12) United States Patent
Shin

(10) Patent No.: US 8,518,661 B2
(45) Date of Patent: Aug. 27, 2013

(54) METHOD OF SELECTING AND SEPARATING NORMAL CELLS AND SPECIFIC CELLS BY USING ULTRASONIC WAVES

(75) Inventor: Sang Mo Shin, Gwangju (KR)

(73) Assignee: Gwangju Institute of Science and Technology, Gwangju (KR)

( * ) Notice: Subject to any disclaimer, the term of this patent is extended or adjusted under 35 U.S.C. 154(b) by 25 days.

(21) Appl. No.: 12/921,097

(22) PCT Filed: Mar. 4, 2009

(86) PCT No.: PCT/KR2009/001076
§ 371 (c)(1),
(2), (4) Date: Sep. 3, 2010

(87) PCT Pub. No.: WO2009/110748
PCT Pub. Date: Sep. 11, 2009

(65) Prior Publication Data
US 2011/0020858 A1    Jan. 27, 2011

(30) Foreign Application Priority Data
Mar. 4, 2008 (KR) .................. 10-2008-0020009

(51) Int. Cl.
*C12Q 1/04* (2006.01)
*C12N 13/00* (2006.01)
*A61K 38/00* (2006.01)

(52) U.S. Cl.
USPC .................. 435/29; 435/173.1; 435/325

(58) Field of Classification Search
USPC ........................... 435/29, 173.1, 325
See application file for complete search history.

(56) References Cited

U.S. PATENT DOCUMENTS

| 4,564,019 A * | 1/1986 | Miwa .................. 600/442 |
| 7,229,411 B2 | 6/2007 | Slayton et al. |
| 7,993,271 B2 * | 8/2011 | Liu et al. .................. 600/437 |
| 2003/0089170 A1 | 5/2003 | Amonette et al. |

FOREIGN PATENT DOCUMENTS

| EP | 0 147 032 B1 | 2/1990 |
| JP | 55-094393 A | 7/1980 |
| JP | 62-064342 A | 3/1987 |
| JP | 63-216548 A | 9/1988 |
| JP | 8-299336 A | 11/1996 |
| KR | 1020060068979 A | 6/2006 |

OTHER PUBLICATIONS

Fujii et al. (Attenuation Coefficient Measurement in the Thyroid. 2003. Journal of Ultrasound Medicine 22: 1067-1073).*
Keshavarzi et al. Attenuation Coefficient and Sound Speed in Human Myometrium and Uterine Fibroid Tumors. Journal Ultrasound Medicine. 2001. 20:473-480.*
Goss et al. Compilation of empirical ultrasonic properties of mammalian tissues. II. J. Acoust. Soc. Am. 1981. 68(1):93-108).*
International Search Repot for PCT/KR2009/001076 filed Mar. 4, 2009.
Written Opinion of the International Searching Authority for PCT/KR2009/001076 filed Mar. 4, 2009.

* cited by examiner

*Primary Examiner* — Karen Cochrane Carlson
*Assistant Examiner* — Natalie Moss

(57) ABSTRACT

The present invention relates to a method of selecting and separating normal cells and specific cells by using ultrasonic waves. More particularly, the present invention relates to a method of selecting and separating normal cells and cancer cells, or normal cells and stem cells by using a difference in attenuation coefficients, speed of sound and so on in normal cells and specific cells obtained when ultrasonic waves are radiated. The method of the present invention is capable of selecting and separating normal cells and specific cells (cancer cells or stem cells) in a simple and efficient manner.

3 Claims, 1 Drawing Sheet

[Figure 1]
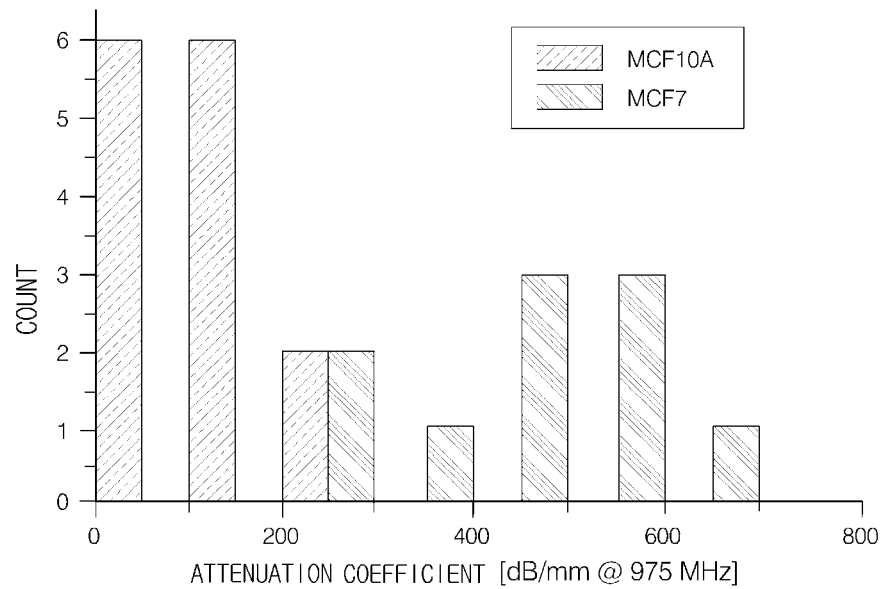
[Figure 2]
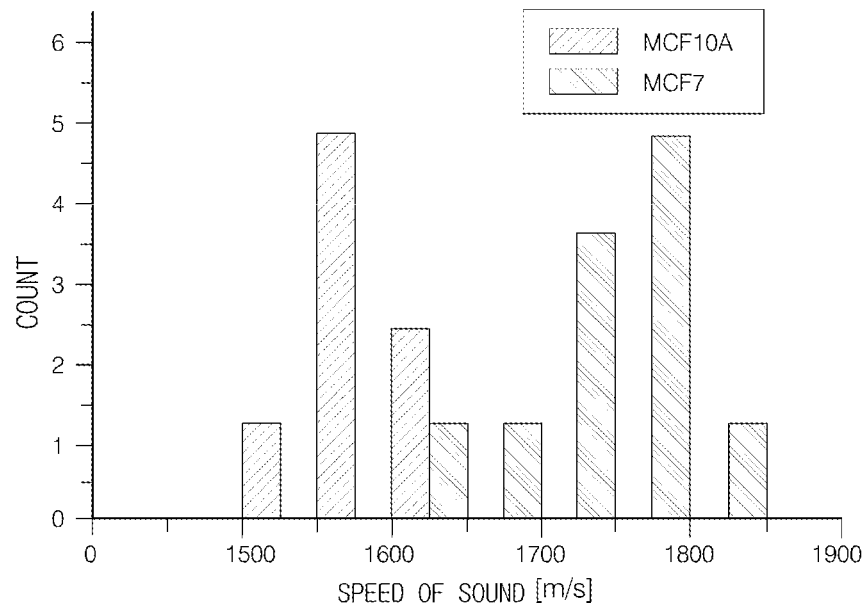

METHOD OF SELECTING AND SEPARATING NORMAL CELLS AND SPECIFIC CELLS BY USING ULTRASONIC WAVES

TECHNICAL FIELD

The present invention relates to a method of selecting and separating normal cells and specific cells by using ultrasonic waves. More particularly, the present invention relates to a method of selecting and separating normal cells and cancer cells, or normal cells and stem cells by using a difference in attenuation coefficients, speed of sound and so on in normal cells and specific cells which are obtained when ultrasonic waves are radiated.

BACKGROUND ART

A sonic wave, which cannot be detected by the human ear and has a frequency range that is more than 20 KHz is referred to as "ultrasonic wave", and the ultrasonic wave is transferred to a far position if the frequency is low, but if the frequency is high, the resolution is improved but the wave is not transferred to the far position.

The ultrasonic wave is widely applied to a medical ultrasonic wave diagnosis system, a flow rate and flow amount measurement system, an ultrasonic wave distance measurement system, a non-contact ultrasonic wave detection device, an ultrasonic wave washing machine, a melting machine, an ultrasonic wave humidifying machine, an ultrasonic wave fat thickness measurement device, an ultrasonic wave pregnancy diagnosis equipment, an ultrasonic wave harmful insect eradication device, an ultrasonic wave nozzle/spray, an ultrasonic wave positioning system, an ultrasonic wave device, an ultrasonic wave, an ultrasonic wave rear detection system and the like.

Korean Registered Patent No. 233352 discloses "a device and method for treating benign prostatic hyperplasia (BPH), prostate cancer and other diseases, which can minimize damage of other tissues in addition to subject tissue and a treating cost by applying condensed ultrasonic wave energy from a probe that is closely positioned around the wound". Korean Patent Laid Open Publication No. 1991-0007487 discloses "a device and method for characterizing amplitude of two or more ultrasonic pulses that are generated from a main ultrasonic wave pulse reflecting from two or more impedance discontinuities that remain while an attenuation coefficient of the reflecting pulse of a radio wave medium that is transferred from a sonic converter to the radio wave medium and has substantially the same reflection coefficient in the medium is not substantially changed".

U.S. Pat. No. 7,229,411 discloses "an ultrasonic wave system for usefully providing imaging, treating and temperature monitoring, which includes a sound transducer (the sound transducer includes a single transducer that is operatably connected to an imaging system, treating system and temperature control system) that is arranged so that the ultrasonic wave system can perform functions of imaging, treating and temperature monitoring". These patent documents and other known documents mention a cancer treating method using an ultrasonic wave converter, an ultrasonic wave image diagnosis machine, and a high strength concentration ultrasonic wave, but do not mention selection and separation of a normal cell and specific cell using ultrasonic waves.

DISCLOSURE

Technical Problem

The present invention has been made in an effort to provide a method for selecting and separating a normal cell and specific cell (cancer cell, tumor cell, or stem cell) by using an ultrasonic wave in a simple and efficient manner.

Technical Solution

The present inventors found that when an ultrasonic wave is radiated, there is a difference between absorption/reflection ratios, attenuation coefficients, speeds of sound, density gradients and the like of a normal cell and a specific cell (cancer cell, tumor cell, or stem cell), thereby providing a method for simply and efficiently selecting and separating the normal cell and cancer cell, or normal cell and stem cell by using the difference between the attenuation coefficients and speeds of sound of the normal cell and specific cell when the ultrasonic wave is radiated.

An exemplary embodiment of the present invention provides a method for selecting and separating a normal cell and a specific cell by using an ultrasonic wave, which includes: (a) radiating the ultrasonic wave that has the same frequency to a plurality of samples that are obtained from a tissue of a specific portion of a mammal including humans; (b) measuring an attenuation coefficient, a speed of sound, or the attenuation coefficient and speed of sound on the basis of the samples to which the ultrasonic wave that has the same frequency is radiated; and (c) selecting and separating the normal cell and specific cell by using the measurement values of the attenuation coefficient, speed of sound, or attenuation coefficient and speed of sound.

In the exemplary embodiment of the present invention, in particular, it is preferable that step (c) includes after classifying a group A of samples in which the measurement values of the attenuation coefficient, speed of sound, or attenuation coefficient and speed of sound are smaller than an average value in respects to whole samples and a group B of samples in which the measurement values of the attenuation coefficient, speed of sound, or attenuation coefficient and speed of sound are higher than the average value in respects to the whole samples, selecting and separating the samples that have measurement values corresponding to the average±standard deviation of the measurement values in respects to the group A and the samples that have measurement values corresponding to the average±standard deviation of the measurement values in respects to the group B.

The ultrasonic wave that is used in the present invention may have a frequency that is more than 20 KHz and it is preferable that it has a frequency of a MHz band or GHz band. As the device for radiating the ultrasonic wave, any one that is known in the art may be used.

The specific cell means a cancer cell, a tumor cell, or a stem cell, and the cancer or tumor may be exemplified by pituitary adenoma, glioma, brain tumor, oral cavity cancer, laryngopharyngeal cancer, chest thymoma, mesothelioma, breast cancer, lung cancer, stomach cancer, esophageal cancer, large intestine cancer, liver cancer, gallbladder carcinoma, cholangiocarcinoma, pancreatic cancer, urothelial carcinoma, ureteral metastases, renal cell carcinoma, testicular tumor, prostate cancer, bladder cancer, uterine cancer, uterine cervix cancer, endometrial cancer, uterine sarcoma, ovarian cancer, malignant lymphoma, Hodgkin's lymphoma, non-Hodgkin's lymphoma, multiple myeloma, acute myelogenous leukemia, acute lymphocytic leukemia, chronic myelogenous leukemia, chronic lymphocytic leukemia, melanoma, skin cancer, thyroid carcinoma, osteoma or the like.

When the density of the medium is $\rho$ and the volume modulus is B, the speed V of the ultrasonic wave may be represented by $(B/\rho)^{1/2}$, and the speed of the ultrasonic wave varies according to the medium. When the ultrasonic wave passes through the medium, a phenomenon where the intensity of ultrasonic wave is lowered by absorption, scattering, reflection and the like of the medium is called attenuation, and the attenuation is affected by the passage length and frequency. The attenuation per unit length is defined by an attenuation coefficient, and the attenuation of the ultrasonic wave is almost linearly increased. An embodiment of the present invention is characterized in that the normal cell and the specific cell (cancer cell, tumor cell, or stem cell) are selected and separated by a significant difference between the attenuation coefficients and/or speeds of sound shown when the ultrasonic wave of the same frequency is radiated. The ultrasonic wave properties such as the attenuation coefficient and/or speed of sound of the normal cells and specific cells are different from each other, and the normal cell and specific cell can be selected and separated by using this.

In addition, the present invention is characterized in that in order to more precisely select and separate the normal cell and the specific by overcoming a limit of measurement error, after a group A of samples in which the measurement values of the attenuation coefficient, speed of sound, or attenuation coefficient and speed of sound are smaller than an average value in respects to whole samples and a group B of samples in which the measurement values of the attenuation coefficient, speed of sound, or attenuation coefficient and speed of sound are higher than the average value in respects to the whole samples are classified, the samples that have measurement values corresponding to the average±standard deviation of the measurement values in respects to the group A and the samples that have measurement values corresponding to the average±standard deviation of the measurement values in respects to the group B are selected and separated. Any one of the samples that have the measurement value that corresponds to average±standard deviation of the measurement value in respects to group A or the samples that have the measurement value that corresponds to average±standard deviation of the measurement value in respects to group B is the normal cell and the other is the specific cell.

In addition, in the method for selecting and separating the normal cell and the specific cell of an exemplary embodiment of the present invention, in addition to the ultrasonic wave property, observed values according to viscoelasticity, IR/UV absorption property, polarization coefficient, reflectivity/refractive index, electrical conductivity, permittivity, capacitance and the like may be more considered.

Advantageous Effects

According to the exemplary embodiment of the present invention, it is possible to select and separate normal cells and specific cells (cancer cells, tumor cells or stem cells) in a simple and efficient manner.

DESCRIPTION OF DRAWINGS

FIG. 1 is a graph that compares an attenuation coefficient of a normal breast cell MCF10A and an attenuation coefficient of a breast cancer cell MCF7 when an ultrasonic wave that has a frequency of 975 MHz is radiated.

FIG. 2 is a graph that compares an ultrasonic wave of a normal breast cell MCF10A and an ultrasonic wave of a breast cancer cell MCF7 when an ultrasonic wave is irradiated.

BEST MODE

Hereinafter, exemplary embodiment of the present invention will be described in detail with reference to the accompanying drawings. However, the present invention has been described in an illustrative manner, and it is to be understood that the terminology used is intended to be in the nature of description rather than limiting. Therefore, many modifications and variations of the present invention are possible in light of the above teachings. Therefore, it is to be understood that within the scope the appended claims, the invention may be practiced otherwise than as specifically described.

Example 1

After the ultrasonic wave that had the frequency of 975 MHz was radiated to a plurality of samples that were obtained from the breast tissue of a human separated, the attenuation coefficient for each sample was measured. There were 6 samples that were formed of the normal cell MCF10A and had the attenuation coefficient of 50 dB/mm or less, 6 samples that had the attenuation coefficient in the range of 100 to 150 dB/mm, and 6 samples that had the attenuation coefficient in the range of 100 to 250 dB/mm. The average of the attenuation coefficient for the samples that were formed of the normal cell MCF10A was 126 dB, and the standard deviation thereof was 67 dB/mm.

Meanwhile, there were 2 samples that were formed of the breast cancer cell MCF7 and had the attenuation coefficient in the range of 250 to 300 dB/mm, 1 sample that had the attenuation coefficient in the range of 350 to 400 dB/mm, 3 samples that had the attenuation coefficient in the range of 450 to 500 dB/mm, 3 samples that had the attenuation coefficient in the range of 550 to 600 dB/mm, and 3 samples that had the attenuation coefficient in the range of 650 to 700 dB/mm. The average of the attenuation coefficient for the samples that were formed of the breast cancer cell MCF7 was 443 dB, and the standard deviation thereof was 129 dB/mm. The level of significance (p value) of the t-test was 0.0001.

Example 2

After the ultrasonic wave that had the frequency of 975 MHz was radiated to a plurality of samples that were obtained from the breast tissue of human separated, the speed of sound for each sample was measured. There were 1 sample that was formed of the normal cell MCF10A and had the speed of sound in the range of 1500 to 1525 m/s, 5 samples that had the speed of sound in the range of 1550 to 1575 m/s, and 2 samples that had the speed of sound in the range of 16000 to 1625 m/s. The average of the speed of sound for the samples that were formed of the normal cell MCF10A was 1583 m/s, and the standard deviation thereof was 24 m/s.

Meanwhile, there were 1 sample that was formed of the breast cancer cell MCF7 and had the speed of sound in the range of 1625 to 1650 m/s, 1 sample that had the speed of sound in the range of 1725 to 1750 m/s, 3 samples that had the speed of sound in the range of 1725 to 1750 m/s, 4 samples that had the speed of sound in the range of 1775 to 1800 m/s, and 1 sample that had the speed of sound in the range of 1825 to 1850 m/s. The average of the speed of sound for the samples that were formed of the breast cancer cell MCF7 was 1,736 m/s, and the standard deviation thereof was 61 m/s. The level of significance (p value) of the t-test was less than 0.0001.

The invention claimed is:

1. A method for selecting and separating a normal cell and a cancer or tumor cell by using an ultrasonic wave, the method comprising:

(a) individually radiating the ultrasonic wave to each of a plurality of sample cells that are obtained from tissue of a portion of a mammal including humans;
(b) measuring an attenuation coefficient, a speed of sound, or the attenuation coefficient and speed of sound on the basis of the sample cells to which the ultrasonic wave is radiated;
(c) classifying a group A of sample cells in which the measured values of the attenuation coefficient, speed of sound, or attenuation coefficient and speed of sound are smaller than an average value with respect to total samples as normal cells, and a group B of sample cells in which the measured values of the attenuation coefficient, speed of sound, or attenuation coefficient and speed of sound are higher than the average value with respect to the total samples as cancer or tumor cells; and
selecting and separating each individual sample cell that has a measurement value corresponding to an average±standard deviation of the measurement values with respect to the group A and samples that have measurement values corresponding to the average±standard deviation of the measurement values in group B to group A or group B respectively.

2. The method for selecting and separating a normal cell and a cancer or tumor cell by using an ultrasonic wave according to claim 1, wherein the ultrasonic wave has a frequency of a MHz band or a GHz band.

3. The method for selecting and separating a normal cell and a cancer or tumor cell by using an ultrasonic wave according to claim 1, wherein the cancer or tumor is pituitary adenoma, glioma, brain tumor, oral cavity cancer, laryngopharyngeal cancer, chest thymoma, mesothelioma, breast cancer, lung cancer, stomach cancer, esophageal cancer, large intestine cancer, liver cancer, gallbladder carcinoma, cholangiocarcinoma, pancreatic cancer, urothelial carcinoma, ureteral metastases, renal cell carcinoma, testicular tumor, prostate cancer, bladder cancer, uterine cancer, uterine cervix cancer, endometrial cancer, uterine sarcoma, ovarian cancer, malignant lymphoma, Hodgkin's lymphoma, non-Hodgkin's lymphoma, multiple myeloma, acute myelogenous leukemia, acute lymphocytic leukemia, chronic myelogenous leukemia, chronic lymphocytic leukemia, melanoma, skin cancer, thyroid carcinoma or osteoma.

* * * * *